United States Patent [19]

Grimard

[11] Patent Number: 5,752,940

[45] Date of Patent: May 19, 1998

[54] SYRINGE AND METHOD FOR LYOPHILIZING AND RECONSTITUTING INJECTABLE MEDICATION

[75] Inventor: Jean Pierre Grimard, Vif, France

[73] Assignee: Becton Dickinson and Company, Franklin Lakes, N.J.

[21] Appl. No.: 628,973

[22] Filed: Apr. 8, 1996

Related U.S. Application Data

[63] Continuation of Ser. No. 187,233, Jan. 25, 1994, abandoned.

[51] Int. Cl.$^6$ .......................... A61M 5/00; A61B 19/00
[52] U.S. Cl. ........................ 604/181; 604/56; 604/82; 604/416; 206/219
[58] Field of Search .................. 604/56, 82, 89, 604/90, 91, 181, 191, 218, 221, 226, 236, 278, 241, 256, 416; 206/219–221

[56] References Cited

U.S. PATENT DOCUMENTS

| | | | |
|---|---|---|---|
| 3,016,896 | 1/1962 | Van Sickle | 604/89 |
| 3,052,240 | 9/1962 | Silver et al. | 604/89 |
| 3,164,303 | 1/1965 | Trautmann | 604/89 X |
| 3,330,281 | 7/1967 | Visser | 215/247 X |
| 3,330,282 | 7/1967 | Visser et al. | 215/247 X |
| 3,901,402 | 8/1975 | Ayres | 215/248 |
| 4,563,174 | 1/1986 | Dupont et al. | 604/89 |
| 4,599,082 | 7/1986 | Grimard | 604/90 |
| 4,613,326 | 9/1986 | Szwarc | 604/89 |
| 4,952,208 | 8/1990 | Lix | 604/187 |
| 5,236,420 | 8/1993 | Pfleger | 604/122 |

FOREIGN PATENT DOCUMENTS

| | | |
|---|---|---|
| 0 302 248 A1 | 2/1989 | European Pat. Off. |
| 2252 951 A | 8/1992 | United Kingdom. |

*Primary Examiner*—Michael Powell Buiz
*Assistant Examiner*—A. T. Nguyen
*Attorney, Agent, or Firm*—Allen W. Wark

[57] ABSTRACT

A syringe assembly includes a substantially cylindrical syringe barrel and a plunger stopper. Distal portions on the plunger stopper are configured to permit outflow of vapor from the syringe barrel during a lyophilization process. Proximal portions of the plunger stopper are dimensioned to engage the syringe barrel in sliding fluid-tight engagement. Liquid medication in the chamber is lyophilized and a vacuum is applied to the syringe barrel after lyophilization. The plunger stopper then is urged distally into sealing engagement with the syringe barrel. A plunger rod can be engaged with the plunger stopper. The tip cap is then removed and a diluent is drawn into the chamber by moving the plunger rod and the plunger stopper in a proximal direction. The syringe assembly then can be used in the standard manner.

20 Claims, 5 Drawing Sheets

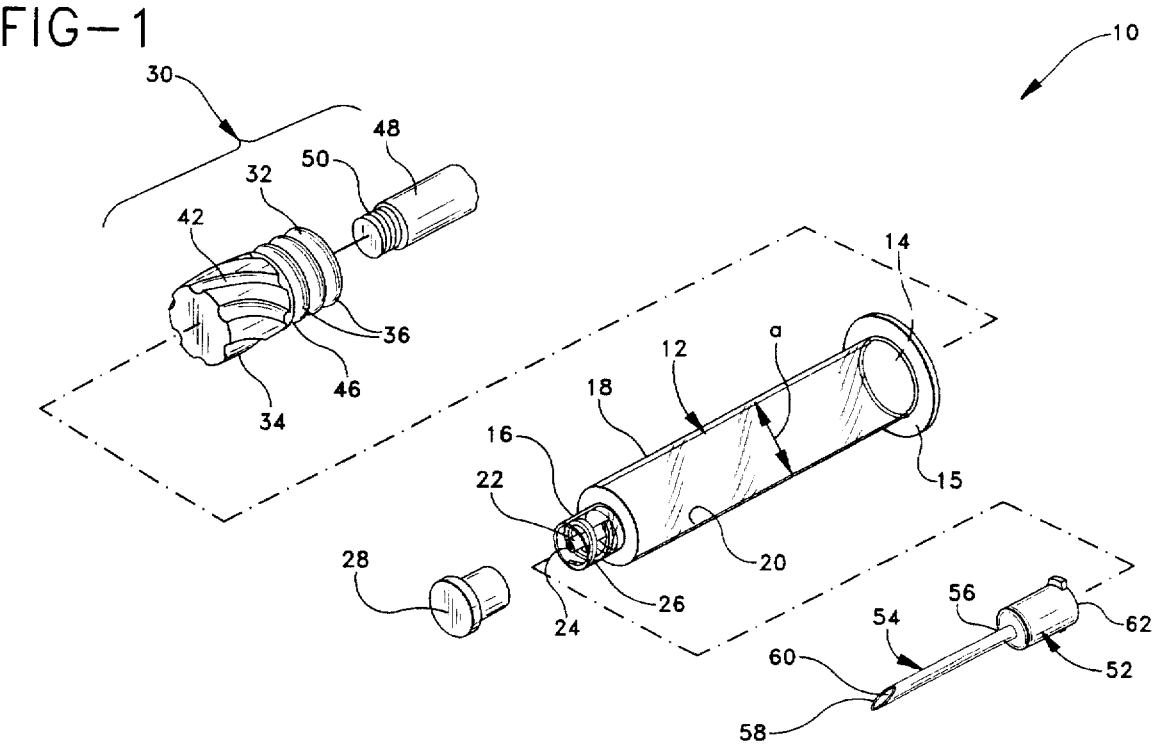

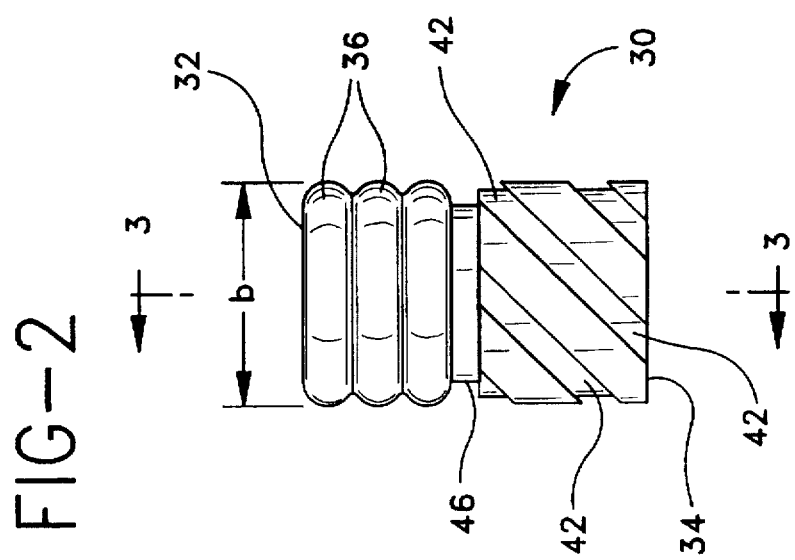
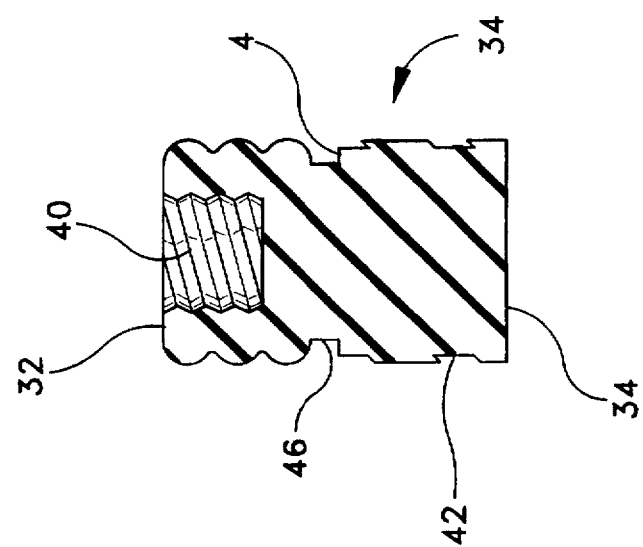
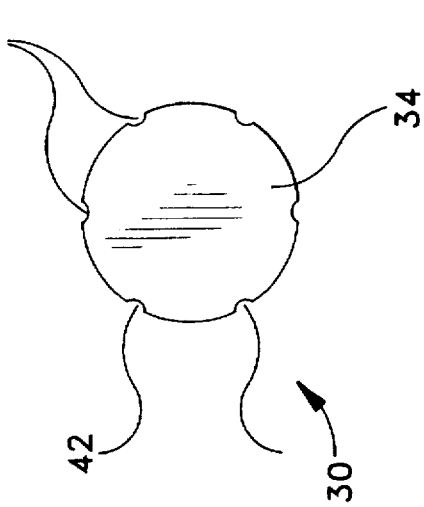
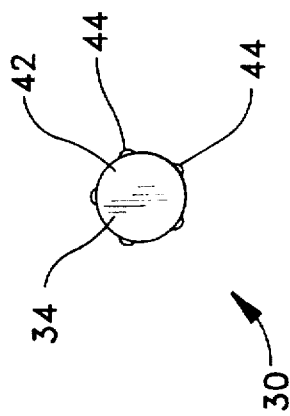

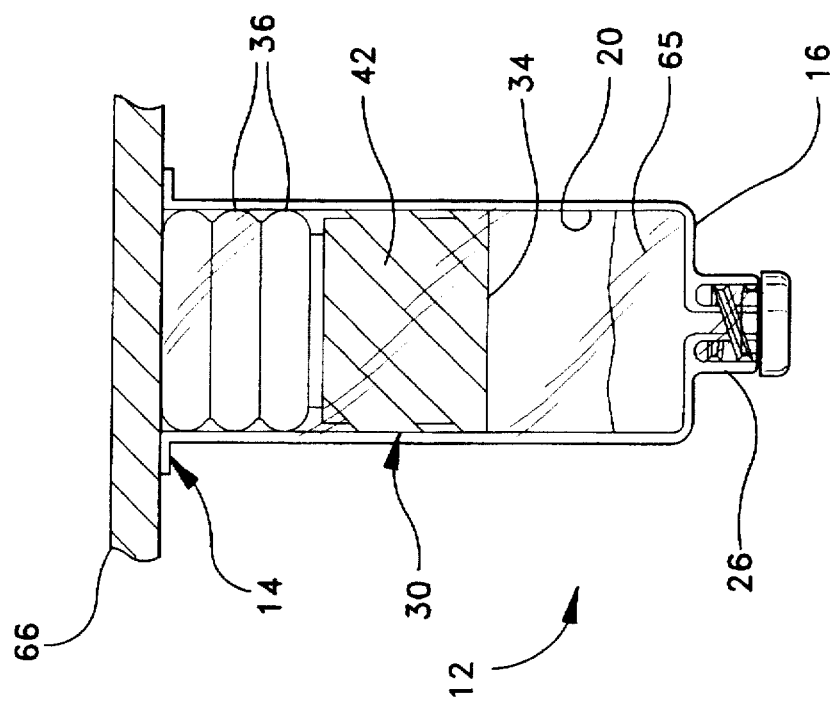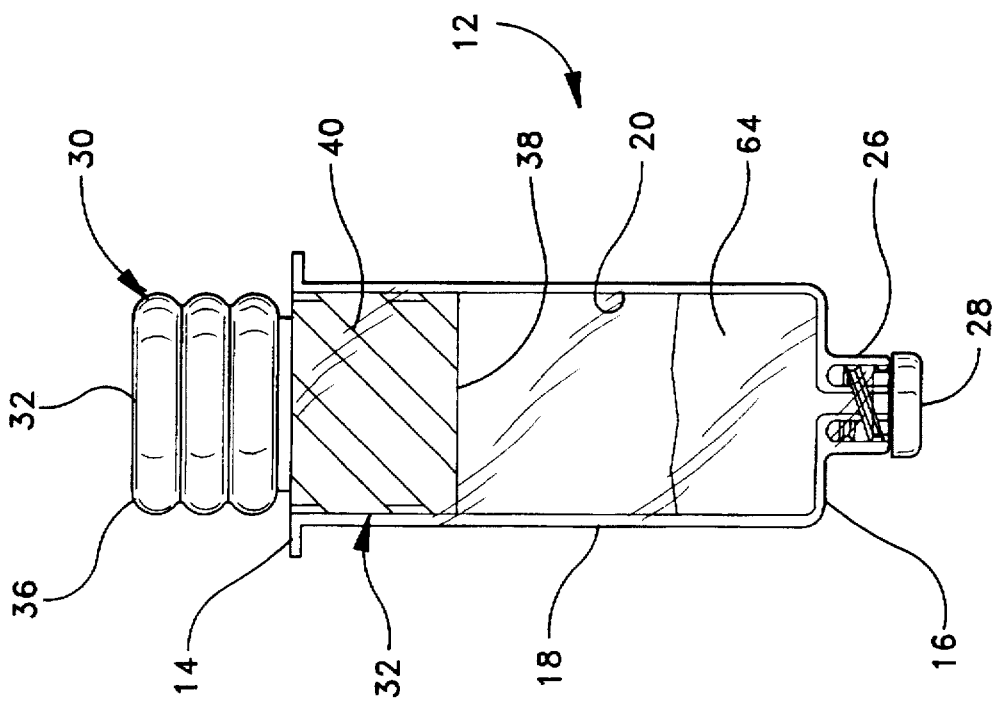

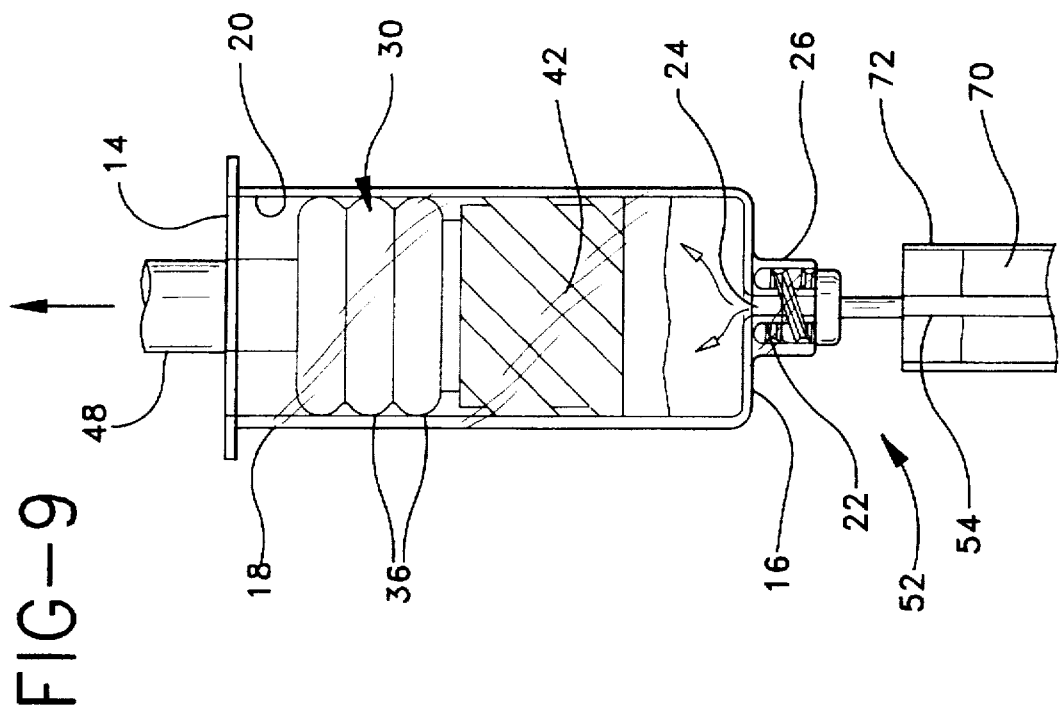
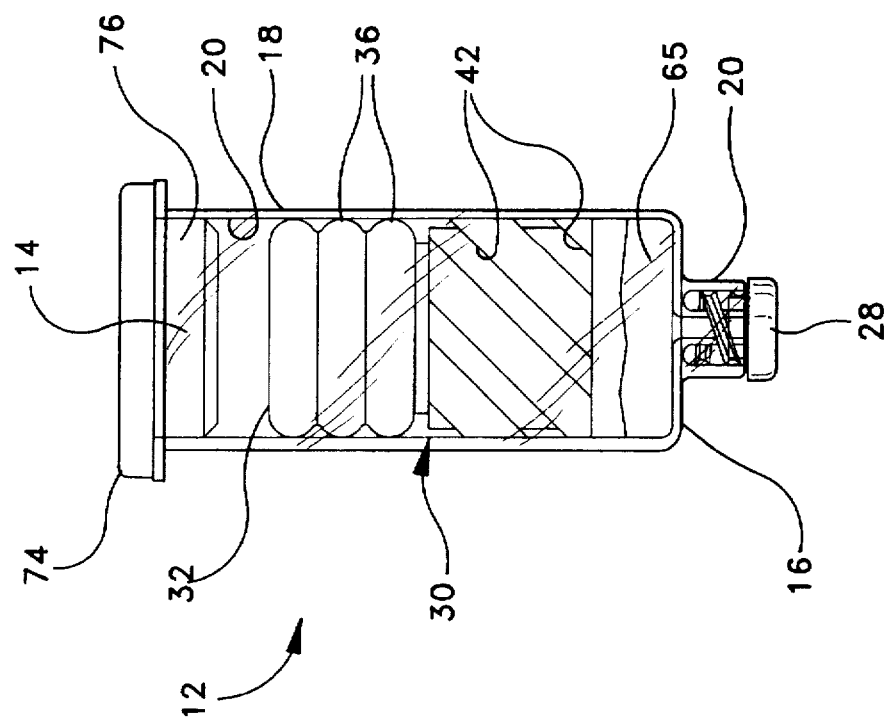

SYRINGE AND METHOD FOR LYOPHILIZING AND RECONSTITUTING INJECTABLE MEDICATION

This application is a continuation of application Ser. No. 08/187,233, abandoned, filed Jan. 25, 1994.

1. FIELD OF THE INVENTION

The subject invention relates to a hypodermic syringe and a method or process for efficiently lyophilizing an injectable medication and for subsequently reconstituting the lyophilized medication.

2. DESCRIPTION OF THE PRIOR ART

Pre-filled hypodermic syringes offer many efficiencies. However, many injectable medications degrade rapidly and lose their effectiveness. Refrigeration and special packaging can increase shelf life, but add to cost, complicate storage and offset many efficiencies provided by pre-filled syringes.

Shelf life can be substantially increased by lyophilizing or freeze drying the injectable medication. The lyophilizing process reduces the liquid medication to a dried powdery or granular form. Lyophilized medication can be stored in the chamber of a hypodermic syringe. Shortly prior to use, the lyophilized medication is mixed with a diluent, and the reconstituted medication can be injected from the same hypodermic syringe in which the lyophilized medication had been stored.

The prior art includes hypodermic syringes made of glass or plastic having a chamber with a stopper slidably disposed at an intermediate position. Regions of the chamber disposed distally of the stopper are of non-cylindrical shape and define a bypass. A lyophilized medication is stored in the chamber distally of the stopper, while a selected diluent is stored in the chamber proximally of the stopper. A plunger is slidably disposed in fluid-tight engagement with the chamber wall proximally of the diluent. Movement of the plunger in a distal direction urges both the diluent and the stopper toward the lyophilized medication. The stopper eventually will align with the bypass region of the prior art syringe barrel, and further movement of the plunger will cause the diluent to flow through the bypass and into the distal portion of the chamber for mixing with the lyophilized medication. The stopper can be configured to promote a flow pattern of the diluent that will enhance mixing of the diluent with the lyophilized medication. An example of such a hypodermic syringe is shown in U.S. Pat. No. 4,599,082.

The two-component hypodermic syringe assembly described above functions very well. However, it is desired to make improvements. For example, the need for two axial spaced chamber sections along the body of the hypodermic syringe necessitates a longer syringe. The lyophilizing process generally is carried out in the syringe. Thus, the lyophilizing apparatus must be large enough to accommodate the larger syringe. Larger hypodermic syringes and correspondingly larger lyophilizing apparatus are more costly and require more space. Additionally, the need for a non-cylindrical cross-section in the bypass region of the prior art syringe increases costs.

SUMMARY OF THE INVENTION

A lyophilizing syringe assembly in accordance with the subject invention includes a generally cylindrical syringe barrel, usually made of plastic or glass, having an open proximal end, a distal end and a fluid receiving chamber therebetween. The distal end of the syringe barrel defines a tip having a passage extending therethrough and communicating with the chamber. A tip cap is releasably engageable with the tip to seal the passage therethrough. The tip also is configured to releasably receive a needle cannula.

The syringe assembly further includes a lyophilizing plunger stopper. The plunger stopper is generally cylindrical and has opposed proximal and distal ends. The stopper is preferably molded from an elastomeric material for sealing engagement with the cylindrical walls of the syringe barrel. The proximal end of the plunger stopper is configured for selective engagement with a plunger rod. For example, a recess may be provided with an array of threads for threadedly engaging a threaded plunger rod. The proximal end of the plunger stopper is further configured for sliding fluid-tight engagement with the cylindrical walls of the syringe barrel. For example, proximal portions of the plunger stopper barrel may include a plurality of annular ribs having diameters slightly greater than the inside diameter of the chamber to sealingly engage the cylindrical chamber wall. The distal end of the stopper defines at least one vapor passage to enable an escape of vapor during a lyophilizing process as defined further herein. The vapor passage may be defined by at least one rib or groove extending from the distal end of the plunger stopper to a point intermediate the opposed distal and proximal ends.

The syringe assembly of the subject invention is employed by attaching the tip cap over the tip of the syringe barrel and depositing a dose of liquid medication in the chamber. The distal end of the plunger stopper then is inserted in the open proximal end of the syringe barrel, such that the vapor passages of the plunger stopper permit fluid flow from the chamber. The syringe barrel is then subjected to a lyophilizing process for freeze drying the liquid portions of the medication in the barrel. The frozen liquid portions of medication are subject to a subatmospheric pressure and then, as a gas or vapor, efficiently drawn through the vapor passages at the distal end of the plunger stopper.

Upon completion of the lyophilizing process, a vacuum is applied in the lyophilizing apparatus to reduce pressure in the chamber. The proximal end of the plunger stopper then is urged into sealing engagement with the cylindrical walls of the syringe barrel. The process continues by permitting regions surrounding the syringe assembly to return to atmospheric pressure. This higher pressure will cause the plunger stopper to move distally in the syringe barrel and toward the lyophilized medication at the distal end of the chamber.

The syringe barrel with the lyophilized medication therein can be packaged and shipped in the standard manner. The lyophilized medication will be safely protected between the tip cap that is sealingly engaged over the tip of the syringe barrel and the plunger stopper that is sealingly engaged within the chamber of the syringe barrel.

The syringe assembly and lyophilized medication can be used by engaging a plunger rod with the engagement means at the proximal end of the plunger stopper. The tip cap can then be removed from the tip of the syringe barrel and a needle cannula can be mounted thereto. The distal tip of the needle cannula then can be inserted into a vial or ampule with an appropriate diluent, and a proximally directed force can be exerted on the plunger rod to move the plunger stopper in a proximal direction. The low pressure created by this proximal movement will cause the diluent to flow through the needle cannula and into the chamber for mixing with the lyophilized medication.

The syringe assembly of the subject invention does not require a bypass in the syringe barrel, and hence can use the less expensive conventional cylindrical syringe barrel. Additionally, by using a diluent from a separate vial or ampule, a separate space for a diluent is not required in the syringe barrel. Thus, the syringe barrel can be substantially shorter than prior art two-component syringe assemblies, and a smaller lyophilizing apparatus also can be used. The subject syringe assembly also requires only one plunger stopper. Hence, further reductions in the size of the syringe barrel can be achieved, along with corresponding cost savings due to the use of a single plunger stopper and a smaller syringe barrel.

BRIEF DESCRIPTION OF THE DRAWINGS

FIG. 1 is an exploded perspective view of a syringe assembly in accordance with the subject invention.

FIG. 2 is a side elevational view of the plunger stopper shown in FIG. 1.

FIG. 3 is a cross-sectional view taken along line 3—3 in FIG. 2.

FIG. 4 is an end elevational view of the plunger stopper shown in FIGS. 2 and 3.

FIG. 5 is an end elevational view similar to FIG. 4 but showing an alternate configuration for the distal end of the plunger stopper.

FIG. 6 is a side elevational view of the syringe assembly in a first operational condition.

FIG. 7 is a side elevational view of the syringe assembly after lyophilizing and stoppering.

FIG. 8 is a side elevational view similar to FIGS. 6 and 7, but showing the syringe assembly after return to atmospheric pressure.

FIG. 9 is a side elevational view similar to FIGS. 6–8, but showing the syringe assembly during reconstitution of the lyophilized medication.

DETAILED DESCRIPTION OF THE PREFERRED EMBODIMENTS

Figure 10:
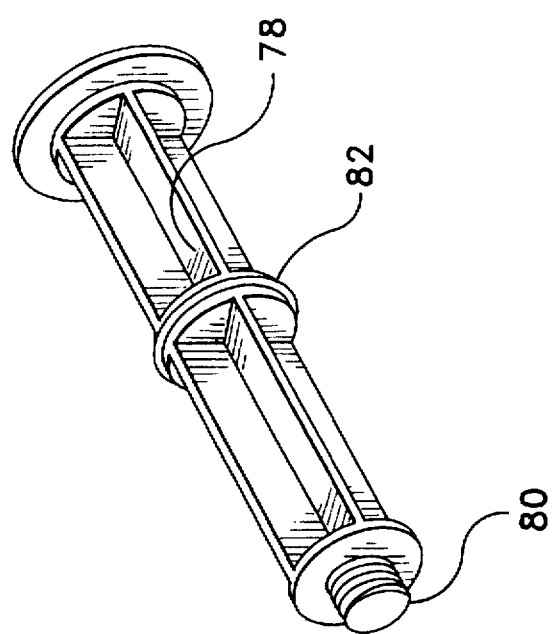
FIG. 10 is an alternative plunger rod construction for use in the syringe assembly.

A syringe assembly in accordance with the subject invention is identified generally by the numeral 10 in FIG. 1. Syringe assembly 10 includes a syringe barrel 12 having an open proximal end 14, a distal end 16 and a substantially cylindrical side wall 18 extending therebetween. The barrel has a uniform circularly shaped cross-section without any deformations in the side wall which allow liquid to flow around stoppers in the barrel. Chamber wall 18 defines a substantially cylindrical fluid receiving chamber 20 of inside diameter "a". Distal end 16 of syringe barrel 12 includes an elongate tip 22 having a passage 24 extending axially therethrough and communicating with chamber 20. A locking luer type collar 26 concentrically surrounds tip 22, and includes an array of threads for threadedly engaging a needle cannula, as explained further herein. Although the locking luer type collar is desirable for enhancing the connection between the needle and the syringe, syringe barrels without locking luer-type collars are frequently used. Syringe barrels without locking collars rely on frictional engagement between the barrel tip and the inside of a needle hub to hold the needle on the barrel.

Syringe assembly 10 includes a tip cap 28 formed from an elastomeric or plastic material and dimensioned for sealingly engaging tip 22 of syringe barrel 12.

The syringe assembly further includes a generally cylindrical plunger stopper 30 with opposed proximal and distal ends 32 and 34 respectively as shown in FIGS. 1–4. The stopper is made of elastomeric material such as natural rubber, synthetic rubber or thermoplastic elastomers. Proximal end 32 of plunger stopper 30 is characterized by a plurality of annular ribs 36 defining an outside diameter "b", which is slightly greater than inside diameter "a" of cylindrical chamber 20 in syringe barrel 12. Thus, ribs 36 can be placed in sliding fluid-tight engagement with cylindrical chamber wall 18 of syringe barrel 12. Proximal end 32 of plunger stopper 30 includes an internally threaded mounting cavity 40 for threadedly receiving a plunger rod as explained herein.

Distal end 34 of plunger stopper 30 includes at least one vapor passage and in this embodiment it includes a plurality of vapor passages 42 extending proximally from distal end 34. The passages may define helical flutes as shown in FIGS. 2 and 4. Alternatively, distal end 34 may be characterized by a plurality of axially extending ribs 44, as shown in FIG. 5, which define vapor passages 42 therealong. The passages extending from distal end 34 of plunger stopper 30 enable an outflow of vapor during lyophilizing processes. The outflow of vapor is further facilitated by a reduced diameter portion 46 intermediate proximal and distal ends 32 and 34.

Returning to FIG. 1, a plunger rod 48 includes a threaded distal end 50 which is threadedly engageable in threaded aperture 40 at distal end 32 of plunger stopper 30. Plunger rod 48 can be threadedly engaged with plunger stopper 30 after lyophilizing the medication and prior to reconstituting the lyophilized medication. It is within the purview of this invention to include other structures for joining the distal end of the plunger rod and the proximal end of the stopper such as snap-fit arrangement or a bayonet-type fitting. The stopper can also include a rigid insert to accept the plunger rod.

The syringe assembly 10 further includes at least one needle assembly 52. Needle assembly 52 includes an elongate needle cannula 54 having a proximal end 56, a distal end 58 and a lumen 60 extending therebetween. Proximal end 56 of needle cannula 54 is securely mounted to a mounting hub 62 which is configured for threaded engagement with luer collar 26 at distal end 16 of syringe barrel 12.

Syringe assembly 10 is used by sealingly engaging tip cap 28 over tip 22 of syringe barrel 12, and then supporting syringe barrel 12 such that proximal end 14 is gravitationally upward, as shown in FIG. 6. For example, the barrel may be supported in the upright position by providing a plate with holes or slots which are larger than the barrel outside diameter but smaller than the finger flange diameter. A selected dose of liquid medication 64 is then deposited in chamber 20 of syringe barrel 12. Distal end 34 of plunger stopper 30 is then inserted into open proximal end 14 of syringe barrel 12 such that reduced diameter portion 46 of plunger stopper 30 is approximately aligned with distal end 14 of syringe barrel 12. Thus vapor passages 42 in plunger stopper 30 enable communication between chamber 20 of syringe barrel 12 and ambient atmosphere surrounding syringe barrel 12. The filled and stoppered syringe barrel is then presented to a lyophilizing apparatus to freeze dry medication 64. Lyophilization process or vacuum converts liquid portions of medication 64 into a solid which is subject to a subatmospheric pressure to create a vapor. The vapor is drawn from chamber 20 through vapor passages 42 and to regions external of the lyophilizing apparatus. The end result is dry lyophilized medication 65.

A vacuum is applied to the lyophilizing apparatus to provide at least a partial vacuum both within chamber 20 and in regions of the lyophilizing apparatus external of syringe barrel 12. Next, as shown in FIG. 7, a solid member such as a shelf 66 of the lyophilizing apparatus is lowered into contact with proximal end 32 of plunger stopper 30 to urge ribs 36, at distal end 32 of plunger stopper 30, into sealing engagement with cylindrical chamber wall 18 of the vertically supported syringe barrel 12. The lyophiling apparatus then is returned to atmospheric pressure. However, the higher atmospheric pressure only affects portions of the lyophilizing apparatus external of chamber 20. The pressure differential on opposed sides of plunger stopper 30 will cause the plunger stopper to slide distally in syringe barrel 12 and toward lyophilized medication 65, as shown in FIG. 8. This distal movement of plunger stopper 30 will terminate when the pressure between the chamber containing the lyophilized medication 65 and plunger stopper 30 approximately equals the atmospheric pressure external of syringe barrel 12.

After the process is complete, the open proximal end of the barrel may be sealed to prevent contamination of the walls of the chamber 20. The sealing can be accomplished with a rubber or plastic plug such as plug 74 which has a boss or projection 76 having a diameter slightly larger than the inside diameter of the chamber. Sealing of the chamber may also be accomplished by additional structure on the syringe plunger rod such as a second stopper-like section on the plunger rod spaced proximally from stopper 30. Such a plunger rod is illustrated in FIG. 10. Plunger rod 78 includes threaded distal end 80 and a central groove having an O-ring 82 which seals the chamber inside diameter while the syringe, containing dry medication, is in storage.

The syringe barrel with the lyophilized medication 65 sealed therein by tip cap 28 and plunger stopper 30 can then be packaged and shipped for subsequent reconstitution and use. Reconstitution is achieved with a diluent 70 as shown in FIG. 9. More particularly, the selected diluent is stored in a container 72 such as a vial, ampule, or any other rigid or flexible reservoir which could be engaged to the barrel tip either directly or through a needle. The diluent 70 is accessed by initially threadedly engaging distal end 50 of plunger rod 48 into threaded aperture 40 of plunger stopper 30. Tip cap 28 is then removed from tip 22 of syringe barrel 12, and hub 62 of needle cannula assembly 52 is threadedly engaged with luer collar 26 of syringe barrel 22. Thus, the lumen through needle cannula 54 is placed in communication with passage 24 through tip 22, and hence in communication with lyophilized medication 65 in chamber 20. Reconstitution is achieved as shown in FIG. 9, by placing distal end 60 of needle cannula 54 in diluent 70. Plunger rod 48 is then moved proximally to draw diluent into chamber 20 for mixing with previously lyophilized medication 65. Syringe assembly 10 then can be used substantially in the standard manner by urging plunger rod 48 in a distal direction. If necessary, the needle assembly 52 used for reconstitution of the lyophilized medication can be removed and replaced with a needle cannula more suitable for injection into a patient. Also, as mentioned hereinabove, it is possible to reconstitute the medication by connecting the barrel directly to a liquid reservoir without the use of a needle.

While the invention has been described with respect to a preferred embodiment, it is apparent that various changes can be made without departing from the scope of the invention as defined by the appended claims. For example, the distal end of the plunger stopper can have vapor passage configurations other than those described herein. Additionally, the plunger stopper may be unitarily molded from an elastomeric material that is suitably configured for engagement with a plunger rod.

What is claimed is:

1. A syringe assembly comprising:

a syringe barrel having an open proximal end, a distal end and a substantially cylindrical chamber wall extending therebetween to define a fluid receiving chamber having an inside surface, a passage extending through said distal end and communicating with said chamber;

means for releasably sealing said passage to isolate said chamber from the environment;

a plunger stopper having opposed proximal and distal ends and an outer surface, at least said distal end of said plunger stopper being disposed in said chamber, at least one vapor passage defined between the inside surface of said chamber wall and said outer surface of said plunger stopper, said vapor passage extending from said distal end of the plunger stopper and terminating at a location between said ends of said stopper, said proximal end of said stopper being dimensioned for sliding fluid-tight sealing engagement with said cylindrical chamber wall so that said distal end of said plunger stopper can be engaged in said chamber with said vapor passage enabling escape of vapor from said chamber during a first lyophilization operation of said injectable medication introduced into the syringe barrel, and said proximal end being dimensioned so that said proximal end of said plunger stopper can be urged into sliding fluid-tight engagement with said cylindrical wall of said chamber upon completion of said lyophilization for sealing the lyophilized medication in said chamber and said plunger stopper subsequently can be urged proximally for a second reconstitution operation of said lyophilized medication into an injectable form; and mounting means defined at said proximal end of said plunger stopper for engaging a plunger rod.

2. The syringe assembly of claim 1, wherein said mounting means of said plunger stopper includes a threaded cavity.

3. The syringe assembly of claim 1, further comprising an elongate plunger rod having proximal and distal ends, said plunger rod selectively engageable with said mounting means of said plunger stopper, said plunger rod being dimensioned to project to locations proximally of said proximal end of said syringe barrel.

4. The syringe assembly of claim 3 further including sealing means on said plunger rod positioned proximally from said distal end of said plunger rod for sealing said chamber from contamination.

5. The syringe assembly of claim 4 wherein said sealing means includes a resilient O-ring around said plunger rod.

6. The syringe assembly of claim 1, wherein said vapor passage is defined by a plurality of axially extending ribs.

7. The syringe assembly of claim 1, wherein said plunger stopper comprises a plurality of circumferentially extending ribs adjacent said proximal end, said circumferentially extending ribs being formed from a resilient material and dimensioned for sealing engagement with said cylindrical chamber wall of said syringe barrel.

8. The syringe assembly of claim 1, further comprising a needle assembly selectively engageable with said distal end of said syringe barrel.

9. The syringe assembly of claim 1 wherein said distal end of said barrel includes a tip projecting distally therefrom and surrounding said passageway.

10. The syringe assembly of claim 1 wherein said means for releasably sealing said passageway is a tip cap sealingly engaging said tip.

11. The syringe assembly of claim 1, wherein said at least one vapor passage includes a plurality of flutes.

12. The assembly of claim 11 wherein said flutes are helically oriented.

13. The syringe assembly of claim 1 further including medication in said chamber.

14. The syringe assembly of claim 13 wherein said medication is lyophilized medication.

15. The syringe assembly of claim 13 further including a plug releasably engaging the open proximal end of the barrel to seal and protect the portion of the barrel chamber between the plunger stopper and the open proximal end of the barrel.

16. The syringe assembly of claim 1 wherein said plunger stopper is made of material selected from the group consisting of natural rubber, synthetic rubber and thermoplastic elastomers.

17. A method for lyophilizing and subsequently reconstituting an injectable medication, said method comprising the steps of:

providing a syringe barrel with an open proximal end, a distal end and a cylindrical chamber wall extending therebetween and defining a fluid receiving chamber having an inside surface, a tip projecting from said distal end of said syringe barrel and having a passage extending therethrough and communicating with said chamber;

sealing said passage in said tip;

placing a liquid medication in said chamber;

providing a plunger stopper having proximal and distal portions and an outer surface, distal portions of said plunger stopper being configured to define at least one vapor passage between the inside surface of said chamber wall of the syringe barrel and the outer surface of said plunger stopper, said proximal portions of said plunger stopper being configured for sliding fluid-tight engagement with said syringe barrel, said proximal end of said stopper including means for engaging a plunger rod;

inserting said distal end of said plunger stopper into said proximal end of said syringe barrel;

subjecting said liquid medication to a lyophilizing operation;

urging said plunger stopper distally into said syringe barrel, such that proximal portions of said plunger stopper seal the lyophilized medication in said chamber;

removing the seal from said tip;

placing the passage of said tip in communication with a diluent; and urging said plunger stopper proximally for drawing a selected amount of said diluent into said chamber for reconstituting said lyophilized medication.

18. The method of claim 17, further comprising the step of subjecting said chamber and regions surrounding said syringe barrel to a vacuum prior to urging said proximal end of said plunger stopper into sealing engagement with said syringe barrel.

19. The method of claim 18, further comprising the step of increasing pressure surrounding said syringe barrel to atmospheric pressure for urging said plunger stopper distally in said syringe barrel and toward said lyophilized medication.

20. The method of claim 17 wherein said step of urging said plunger stopper proximally includes the steps of providing a plunger rod, and engaging said plunger rod with said plunger stopper after urging the plunger stopper toward said lyophilized medication in said syringe barrel.

* * * * *